United States Patent
Gao et al.

(10) Patent No.: US 10,294,526 B2
(45) Date of Patent: May 21, 2019

(54) POLYMER CO-LOCATION IN SURFACE-ATTACHED BIOPOLYMERS AND ARRAYS OF BIOPOLYMERS

(71) Applicant: Intel Corporation, Santa Clara, CA (US)

(72) Inventors: Yuan Gao, Mountain View, CA (US); Gunjan Tiwari, Sunnyvale, CA (US)

(73) Assignee: Intel Corporation, Santa Clara, CA (US)

( * ) Notice: Subject to any disclaimer, the term of this patent is extended or adjusted under 35 U.S.C. 154(b) by 69 days.

(21) Appl. No.: 15/687,758

(22) Filed: Aug. 28, 2017

(65) Prior Publication Data

US 2017/0356044 A1 Dec. 14, 2017

Related U.S. Application Data

(62) Division of application No. 14/244,288, filed on Apr. 3, 2014, now Pat. No. 9,745,628, which is a division
(Continued)

(51) Int. Cl.
*C40B 40/00* (2006.01)
*C12Q 1/6876* (2018.01)
(Continued)

(52) U.S. Cl.
CPC ........ *C12Q 1/6876* (2013.01); *B01J 19/0046* (2013.01); *C40B 50/18* (2013.01); *C40B 80/00* (2013.01); *B01J 2219/00596* (2013.01); *B01J 2219/00608* (2013.01); *B01J 2219/00626* (2013.01); *B01J 2219/00653* (2013.01); *B01J 2219/00702* (2013.01); *B01J 2219/00722* (2013.01); *B01J 2219/00725* (2013.01); *C40B 40/00* (2013.01); *C40B 40/06* (2013.01)

(58) Field of Classification Search
None
See application file for complete search history.

(56) References Cited

U.S. PATENT DOCUMENTS 5,352,574 A 10/1994 Guiseppi-elie
5,552,270 A 9/1996 Khrapko et al.
(Continued)

OTHER PUBLICATIONS

"U.S. Appl. No. 14/244,288, Examiner Interview Summary dated Apr. 7, 2017", 2 pgs.
(Continued)

*Primary Examiner* — Christian C Boesen
(74) *Attorney, Agent, or Firm* — Schwegman Lundberg & Woessner, P.A.

(57) ABSTRACT

Embodiments of the present invention provide substrates having controllably co-located polymers of different sequences. Methods are provided that allow the fabrication of arrays of polymers on a substrate having controllably co-located polymers in regions of the array. For example, polymers of nucleic acids and peptides having different sequences and or compositions can be co-located within a region of a substrate. Also provided are arrays of DNA polymers wherein polymers having two different sequences are co-located within a region of an array. The co-located DNA polymers can comprise complementary DNA that is able to hybridize and form double stranded DNA. Arrays having regions comprising double stranded DNA are provided.

8 Claims, 7 Drawing Sheets

Related U.S. Application Data of application No. 12/217,097, filed on Jun. 30, 2008, now Pat. No. 8,697,605.

(51) Int. Cl.
  *B01J 19/00* (2006.01)
  *C40B 50/18* (2006.01)
  *C40B 80/00* (2006.01)
  *C40B 40/06* (2006.01)

(56) References Cited

U.S. PATENT DOCUMENTS

| | | | |
|---|---|---|---|
| 5,653,939 | A | 8/1997 | Hollis et al. |
| 5,766,934 | A | 6/1998 | Guiseppi-Elie |
| 5,874,219 | A | 2/1999 | Rava et al. |
| 6,093,302 | A | 7/2000 | Montgomery |
| 6,121,048 | A | 9/2000 | Zaffaroni et al. |
| 6,258,606 | B1 | 7/2001 | Kovacs |
| 6,280,595 | B1 | 8/2001 | Montgomery |
| 6,444,111 | B1 | 9/2002 | Montgomery |
| 6,456,942 | B1 | 9/2002 | Anderson |
| 6,518,022 | B1 | 2/2003 | Sosnowski et al. |
| 6,566,495 | B1 | 5/2003 | Fodor et al. |
| 6,682,936 | B2 | 1/2004 | Kovacs |
| 6,867,048 | B2 | 3/2005 | Kovacs |
| 7,622,295 | B2 | 11/2009 | Cabezas |
| 7,923,237 | B2 | 4/2011 | Castro et al. |
| 8,614,086 | B2 | 12/2013 | Holt et al. |
| 9,745,628 | B2 | 8/2017 | Gao et al. |
| 2006/0275927 | A1 | 12/2006 | Dubin et al. |
| 2007/0292855 | A1 | 12/2007 | Dubin et al. |
| 2008/0157786 | A1 | 7/2008 | Holt et al. |
| 2008/0160635 | A1 | 7/2008 | Castro et al. |
| 2009/0000957 | A1 | 1/2009 | Dubin et al. |
| 2014/0213484 | A1 | 7/2014 | Gao et al. |

OTHER PUBLICATIONS

"U.S. Appl. No. 14/244,288, Notice of Allowance dated Apr. 11, 2017", 9 pgs.

"U.S. Appl. No. 14/244,288, Preliminary Amendment filed Apr. 3, 2014", 6 pgs.

"U.S. Appl. No. 14/244,288, Response filed Mar. 20, 2017 to Restriction Requirement dated Jan. 18, 2017", 4 pgs.

"U.S. Appl. No. 14/244,288, Restriction Requirement dated Jan. 18, 2017", 11 pgs.

Benters, "", Nucleic Acids Research vol. 30, (2002), 1-7.

Brockman, "", Journal of the American Chemical Society vol. 121, (Aug. 19, 1999), 804-8051.

Carbone, Giuseppina, et al., "DNA binding and antigene activity of a daunomycinconjugated triplex-forming oligonucleotide targeting the P2 promoter of the human c-myc gene", Research, 2004, vol. 32, No. 8, (2004), 2396-2410.

Diviacco, Silvia, et al., "Site-directed inhibition of DNA replication by triple helix formation", The FASEB Journal, (2001), 2660-2668.

Egeland, Ryan D, et al., "An Electrochemical Redox Couple Activitated by Microelectrodes for Confined Chemical Patterning of Surfaces", Analytical Chemistry, vol. 74, No. 7, (Apr. 1, 2002), 1590-1596.

Fedurco, "", Nucleic Acids Research vol. 34, (Feb. 9, 2006), 1-13.

Goncaleves, D., et al., "Label-free Electronic Detection of Biomolecules Using A-Si:H Field-effect Devices", Journal of Non-Crystalline Solids 352, (Apr. 4, 2006), 2007-2010.

Guiducci, C, et al., "A Biosensor for Direct Detection of DNA Sequence Based on Capacitance Measurements", (Dec. 28, 2006).

Guiducci, C, et al., "DNA detection by integrable electronics", Biosensors and Bioelectronics 19, (2004), 781-787.

Lmmoos, "", Journal of the American Chemical Society vol. 126, (Aug. 17, 2004), 10814-10815.

Maurer, K, et al., "Electrochemically Generated Acid and Its Containment to 100 Micron Reaction Areas for the Production of DNA Microarrays", PLoS One 1 (1): e34. doi:1 0.137/journal.pone/00000034, (2006), 1-7.

Pouthas, F, et al., "Spatially Resolved Electronic Detection of Biopolymers", Physical Review E 70, 031906, (Sep. 21, 2004), 031906-1-031906-8.

Shchepinov, et al., "", Nucleic Acids Research vol. 25, (1997), 1155-1161.

Shumaker-Parry, "", Analytical Chemistry vol. 76, (Mar. 4, 2004), 2071-2082.

Steemers, et al., "", Nature Biotechnology vol. 18, (Jan. 2000), 91-94.

U.S. Appl. No. 11/641,244, U.S. Pat. No. 7,622,295, filed Dec. 9, 2006, Molecular Microarrays and Helical Peptides.

U.S. Appl. No. 11/646,602, U.S. Pat. No. 7,923,237, filed Dec. 28, 2006, Method and Apparatus for Combined Electrochemical Synthesis and Detection of Analytes.

U.S. Appl. No. 11/646,600, U.S. Pat. No. 8,614,086, filed Dec. 28, 2006, Quality Control Methods for the Manufacture of Polymer Arrays.

U.S. Appl. No. 11/646,615, U.S. Pat. No. 8,999,724, filed Dec. 28, 2006, Method and Apparatus for Match Quality Analysis of Analyte Binding.

U.S. Appl. No. 12/217,097, U.S. Pat. No. 8,697,605, filed Jun. 30, 2008, Polymer Co-Location in Surface-Attached Biopolymers and Arrays of Biopolymers.

U.S. Appl. No. 14/244,288, U.S. Pat. No. 9,745,628, filed Apr. 3, 2014, Polymer Co-Location in Surface-Attached Biopolymers and Arrays of Biopolymers.

POLYMER CO-LOCATION IN SURFACE-ATTACHED BIOPOLYMERS AND ARRAYS OF BIOPOLYMERS

CROSS REFERENCE TO RELATED APPLICATIONS

This present application is a division of application Ser. No. 14/244,288, filed Apr. 3, 2014, which is a division of application Ser. No. 12/217,097, filed Jun. 30, 2008. The present application is related to U.S. Pat. No. 7,923,237, entitled "Method and Apparatus for Combined Electrochemical Synthesis and Detection of Analytes," filed Dec. 28, 2006, U.S. Pat. No. 8,999,724, entitled "Method and Apparatus for Match Quality Analysis of Anyalyte Binding," filed Dec. 28, 2006, U.S. Pat. No. 8,614,086, entitled "Quality Control Methods for the Manufacture of Polymer Arrays" filed Dec. 28, 2006, and U.S. Pat. No. 7,622,295, entitled "Molecular Microarrays and Helical Peptides" filed Dec. 19, 2006, the disclosures of which are incorporated by reference in the disclosure of this application.

BACKGROUND OF THE INVENTION

1. Field of the Invention

Embodiments of the present invention relate polymer compositions on the surface of a substrate and methods of creating varied polymer compositions on the surface of a substrate, and additionally to arrays of polymers having varied compositions within a region of the array, to arrays of nucleic acid polymers, to arrays of peptides, and to methods of making arrays of polymers having controllably co-located polymers of different sequences.

2. Background Information

Microarrays of nucleic acids, peptides, proteins, and oligosaccharides continue to gain importance as powerful tools for research and diagnostic applications in the biomedical sciences. Nucleic acid microarrays, for example, can be used to monitor gene expression and genetic mutations in a massively parallel manner. Proteinaceous microarrays provide the ability, for example, to characterize the molecular progression of disease, research cellular pathways, and perform high throughput screening in drug discovery applications. The ability to collect large volumes of information is an integral part of biomarker discovery and personalization of medical treatments. Further, other applications in bioscience, such as for example, the analysis of the proteomic content of an organism, disease detection, pathogen detection, environmental protection, food safety, and biodefense are capable of benefiting from tools that allow rapid multiplexed interrogation of analyte samples.

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), a phosphate group, and one of five bases, adenine (A), cytosine (C), guanine (G), and thymine (T) or uracil (U). The human genome, for example, contains approximately three billion nucleotides of DNA sequence and an estimated 20,000 to 25,000 genes. DNA sequence information can be used to determine multiple characteristics of an individual as well as the presence of and or suceptibility to many common diseases, such as cancer, cystic fibrosis, and sickle cell anemia.

As the genomic and proteomic knowledge base expands, so does the need for methods to collect, understand, and apply biologically relevant information. The drive towards personalized medicine magnifies these needs. Methods, such as analyses using microarrays that allow the use of small volumes of sample for highly multiplexed analysis of a plurality of components are valuable tools. Methods that provide for the controllable automated manufacture of arrays derive value from these same biomedical detection and analysis goals.

DETAILED DESCRIPTION OF THE INVENTION

Embodiments of the invention provide methods for creating polymers on the surface of a substrate and substrates having polymers attached to their surface. Methods according to embodiments are useful for large scale synthesis techniques and for large scale multiplexed synthesis techniques that are used to create arrays of polymers on a substrate. Methods can be used to form regions on a substrate having two different polymers co-located within the region. Methods described herein can be used to create, for example, arrays having complementary double stranded DNA (dsDNA) on the surface of a substrate. A variety of combinations of co-located polymers are possible, such as, for example, a peptide and an antibody, two more peptides, a DNA strand and a DNA binding protein, a carbohydrate and a peptide, or a carbohydrate and an antibody The methods are useful for example, for creating substrates and arrays having co-located species using automated synthesis reactions. Substrates and arrays are provided having a variety of polymers attached to a surface.

Double stranded DNA that is attached to the surface of a substrate through a single linker molecule provides duplex DNA that is potentially more stable toward dehybridization forces than dsDNA that has been attached to the surface through other types of attachment procedures. More randomized procedures for attaching DNA and other types of bio-polymers typically provide little control over the section of the molecule that becomes attached to the substrate, in what orientation the molecule is attached to the substrate (sometimes providing non-functional molecules because the functional piece of the molecule is blocked by the proximity of the substrate through steric interactions), and randomized co-locations that may or may not provide molecules co-located with the desired proximity.

Arrays having a variety of double-stranded DNA molecules immobilized in regions of the array are created. Arrays of DNA that provide immobilized dsDNA are useful platforms for high-throughput anti-gene agent screening and can be powerful tools for drug discovery applications. A large array allows a large number of dsDNA sequences to be screened. Additionally, DNA arrays having dsDNA immobilized in regions can be used to analyze activity-conformation relationships between dsDNA and synthetic or natural ligands, such as for example, peptides, small molecules, carbohydrates, and chimeric molecules. Further, electronic detection platforms provide advantages of enabling label-free detection of molecular interaction events providing for simplification of assay procedures.

Figure 1:
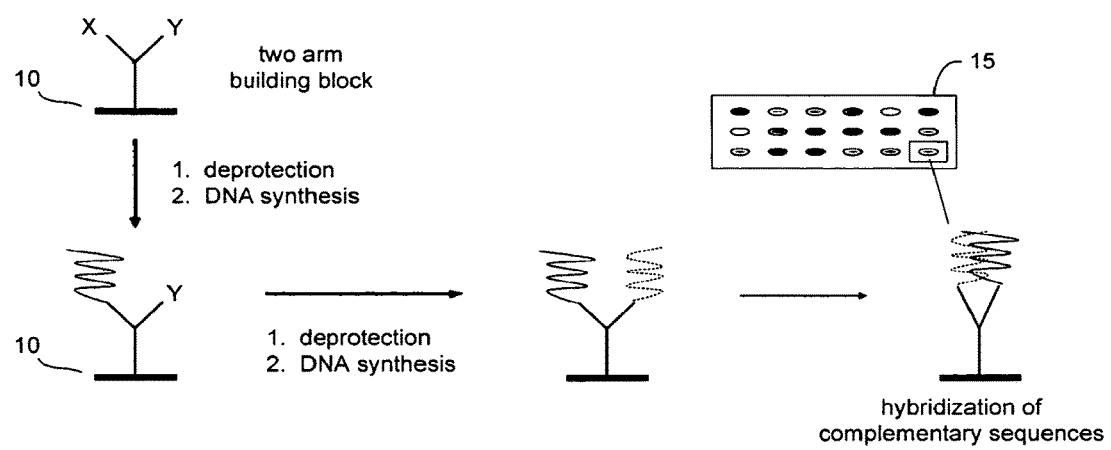
FIG. 1 provides a scheme whereby two polymers having different sequences and or compositions can be controllably co-located in a region on a substrate.

A method for creating a region on a substrate having attached co-located complementary double stranded DNA is diagrammed in FIG. 1. In FIG. 1, a substrate 10 has a molecule attached that is a two arm building block (or trifunctional molecule). A trifunctional molecule has three functional regions, one capable of attaching to the surface of a substrate, and two more regions (arms) that are capable of attaching to polymers. In FIG. 1, the trifunctional building block is attached to the substrate surface and the reactive functionalities of the two arms are protected by protecting groups X and Y. One of the two protecting groups is selectively removed (in this example X is removed and Y remains attached to the two arm building block and protects the second arm from undergoing undesired chemical reactions), and a DNA molecule is synthesized at (or attached to) the site of deprotection on one arm of the trifunctional linker. The first DNA molecule is terminated with a group that prevents further polymer synthesis (or attachment) under DNA synthesis conditions. The second protecting group is then removed (in this case, the Y group), and a second DNA polymer is synthesized on (or attached to) the second arm of the two arm building block. In this case, the second DNA strand is chosen to be complementary to the first DNA strand and is capable of hybridizing to the first DNA strand. The hybridized DNA strands provide dsDNA in a region on the substrate surface. The method according to FIG. 1 is capable of being used to synthesize arrays 15 of co-located polymers and arrays of both co-located polymers and single sequence polymers. Methods for DNA and other polymer synthesis are described more fully herein.

Polymers may be attached to the arms of the two-arm building block through coupling reactions between the polymer and the deprotected reactive group on the two arm building block. Polymers may be increased in length or otherwise modified after coupling to the surface of the substrate through the trifunctional molecule. Optionally, one or both of the polymers may be synthesized through well-known solid-phase synthesis techniques (such as for peptides and nucleic acids) and as described more fully herein. If an array is being synthesized, after a first polymer is synthesized on a first arm of the two arm building block, the second arm can be deprotected by exposing the surface of the array to a deprotecting agent and coupling a monomer unit, such as a nucleic acid, having a protecting group that is removable under different conditions than the conditions used to remove the protecting group on the second arm of the two arm building block. The protecting group on the monomer coupled to the second arm after deprotection of the second arm can be removable under conditions that allow selective activation of sites on an array toward polymer synthesis. The two-arm building block can be attached to the substrate through a variety of methods and linking molecules as is well known in the art and as described herein. Linking molecules are also optionally attached to the arms of the two arm building block before the addition of functional polymers (e.g., polymers providing biologic activity, molecular recognition activity, or other desired properties in analysis reactions).

Figure 2:
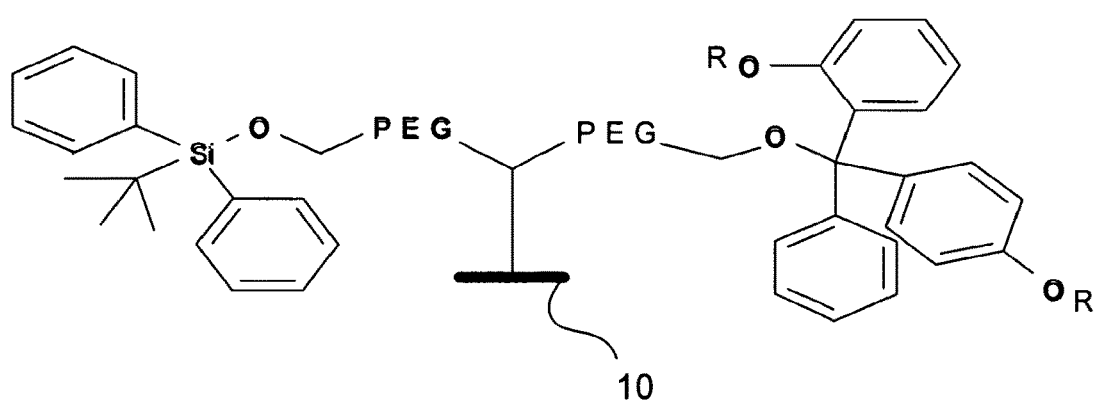
FIG. 2 provides an exemplary molecule attached to a substrate that can be used to create a region on a substrate having two different molecules or polymers located within the one region.

FIG. 2 provides a schematic of a two arm building block attached to a substrate 10 that has two different protecting groups attached to the arms of the building block. Additionally, the two arms are provided with two polyethylene glycol linkers (labeled PEG in FIG. 2) that extend the linker molecule arms above the substrate surface and can function to reduce steric constraints between molecules that are attached to the arms of the two arm building block. The PEG spacer provides flexibility to the immobilized structure in aqueous solutions. The length of the PEG spacer can be chosen to optimize desired properties of the array, such as DNA synthesis and binding performance. In the example shown in FIG. 2, the protection orthogonal, so that one arm can be selectively deprotected while the other arm remains screened from reactivity. The first protecting group, dimethoxytrityl (DMT), on one arm is acid-labile and can be removed (or deprotected), for example, using an acid such as an electrochemically generated acid (EGA). The protecting group on the other arm is tert-butyl diphenyl silane (TBDPS) which is stable to acids such as EGAs, but can be removed using tert-butyl ammonium fluoride (TBAF). Thus, the example in FIG. 2 provides a system in which one arm of the two arm building block can be selectively activated toward molecular synthesis or attachment while the other arm remains protected and unreactive.

In general, two arm building blocks are a trifunctional molecule that has three functional sites, one site is capable of attaching to a substrate surface, and two sites (or arms) are available for further molecular attachment after the attachment of the two arm building block to the substrate surface. Trifunctional molecules are molecules such as, for example, $CHR^1R^2R^3$ wherein $R^1$, $R^2$, and $R^3$ are alkanes having 0 to 20 carbon atoms and a functional group such as —OH or —NH$_2$ that provides a site for further molecular attachment. Additional molecules that are useful as two arm building blocks include, for example, sugars such as, arabinose, ribose, ribulose, xylose, xylulose, lyxose, allose, altrose, fructose, galactose, glucose, gulose, idose, mannose, sorbose, talose, tagatose, and sedoheptulose. Sugar molecule two arm building blocks can be protected with a phosphoramidite by reacting a sugar molecule having one hydroxyl protected with tert-butyl-di-phenylsilane and one hydroxyl protected with DMT 2-cyanoethyl-N,N-diisopropylchlorophosphoramidite, diisopropylethylamine, THF, −78 to 25° C. (reagents are available from Sigma-Aldrich, St. Louis, Mo.). Molecules that are useful as two arm building blocks additionally include, for example, 2,4-diamino 1-propionic acid, diaminobutanoic acid. Many orthogonally protected bifurcation molecules, such as TRT-diaminopropionic acid (FMOC)—OH (TRT is triphenylmethyl or trityl and FMOC is fluorenylmethoxycarbonyl and is base-cleavable) and FMOC-diaminobutanoic acid (MTT)-OH (MTT is 4-methyltrityl, an acid-removable protecting group) are commercially available from, for example, EMD Biosciences Nova Biochem, La Jolla, Calif.; Bachem, Torrance, Calif.; and Chem-Impex International. Additional examples include, C3 Spacer Amidite (DMT-1,3-Propanediol), Spacer 9 Amidite (DMT-Tri(ethylene glycol)) and Spacer 18 Amidite (DMT-Hexa(ethylene glycol)) available from Biosearch Technologies, Novato, Calif.

A protecting group is a group which is bound to a molecule and designed to block a reactive site in a molecule, but may be removed upon exposure to an activator, such as electromagnetic radiation, or a deprotecting reagent. Deprotecting reagents include, for example, acids, bases, and TBAF. Protecting groups can be bound to a monomer, a polymer, a linker molecule or a monomer, or polymer, or a linker molecule attached to a solid support to protect a reactive functionality on the monomer, polymer, or linker molecule.

Orthogonal protection schemes provide the ability to selectively activate one arm of a two arm building block toward molecular attachment or synthesis while maintaining a second (third, fourth, etc.) as protected and unreactive toward molecular attachment and synthesis. Orthogonal protection schemes typically use a protecting group that is removable under a first condition but not under a second condition in conjunction with a protecting group that is removable under the second condition. Higher order orthogonal protection is possible whereby three (or more) different protecting groups are used that are removable under three different conditions and two protecting groups are non-removable under two of the three conditions (and similarly for greater than three protecting groups). In orthogonal protection applications for DNA synthesis and two-arm linkers, orthogonal protecting groups useful in DNA synthesis include dimethoxytrityl (DMT), which is acid labile, and triisopropyl silane (TIPS) and tert-butyl diphenyl silane (TBDPS), which are stable to acid and base but which are removable with TBAF.

Some examples of wavelength controlled orthogonal protecting groups are described in "Wavelength-Controlled Orthogonal Photolysis of Protecting Groups," Blanc, A. and Bochte, C., *J. Org. Chem.*, 67:5567 (2002). Additional examples of photo-cleavable protecting groups can be found in: *Photogenerated Reagents in Biochemistry and Molecular Biology*, Bayley, H., Laboratory Techniques in Biochemistry and Molecular Biology, 12, Elsevier (2002); and Clark, M. A. and Romoff, T. T., Synthesis of peptides and peptidomimetics, *Methods of Organic Chemistry*, E22a:276 (2004). The most common photocleavable groups are 2-nitrobenzyl-derived carbamates, esters, and ethers. Examples include Z(2-NO2), nitroveratryloxycarbonyl (NVOC), NDMOC, di(nitrobenzyl)hydroxymethyl (DNBOC), Menpoc, .alpha.-dimethyl-dimethoxybenzyloxycarbonyl (DDZ). Other examples include tosyl, phenacyl-based esters, and the 5-bromo-7-nitro-indolinyl group. Many amino acids with photocleavable protecting groups are available from Chem-Impex International, Wood Dale, Ill.

In orthogonal protection schemes for amino acids, peptide bond forming amine groups are preferably protected by t-butoxycarbonyl (t-BOC or BOC) or benzyloxycarbonyl (CBZ), both of which are acid labile, or by 9-fluorenyl-methoxycarbonyl (FMOC), which is base labile. Amino acid building blocks having reactive groups in addition to the peptide forming sites can be protected from reactivity with protecting groups. For example, the a-amino group of an amino acid can be protected with an N-protecting group to prevent unwanted reactivity. If necessary, a side chain of the building block (for example, an R group of an amino acid) may also have a protecting group. Suitable protecting groups include, for example, t-butoxycarbonyl (t-BOC), and fluorenylmethoxycarbonyl (FMOC), and 2-(4-biphenylyl)-2-oxycarbonyl.

Additional protecting groups that may be used in accordance with embodiments of the invention include acid labile groups for protecting amino moieties: tert-amyloxycarbonyl, adamantyloxycarbonyl, 1-methylcyclobutyloxycarbonyl, 2-(p-biphenyl)propyl(2)oxycarbonyl, 2-(p-phenylazophenyl)propyl(2)oxycarbonyl, alpha., .alpha.-dimethyl-3,5-dimethyloxybenzyloxy-carbonyl, 2-phenylpropyl(2)oxycarbonyl, 4-methyloxybenzyloxycarbonyl, furfuryloxycarbonyl, triphenylmethyl(trityl), p-toluene-sulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9-fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl(hydrazine), trifluoroacetyl(piperidine), and chloroacetyl (2-aminothiophenol); acid labile groups for protecting carboxylic acids: tert-butyl ester; acid labile groups for protecting hydroxyl groups: dimethyltrityl. See also, Greene, T. W., *Protective Groups in Organic Synthesis*, Wiley-Interscience, NY, (1981).

An array is an intentionally-created collection of molecules housed on a solid support in which the identity or source of a group of molecules is known based on its location on the array. The molecules housed on the array and within a feature of an array can be identical to or different from each other. A macroarray generally contains feature sizes of about 300 µm or larger and can be imaged by gel and blot scanners. A micro array generally has feature sizes of less than 300 µm.

The features, regions, spots, or sectors of an array may have any convenient shape, for example, circular, square, rectangular, elliptical, or wedge-shaped. In some embodiments, the region in which each distinct molecule is synthesized within a sector is smaller than about 1 mm$^2$ or less than 0.5 mm$^2$. In further embodiments the regions have an area less than about 10,000 µm$^2$ or less than 2.5 µm$^2$. Additionally, multiple copies of a polymer are located within any region. The number of copies of a polymer can be in the thousands to the millions or more within a region, depending in part on the size of the region. In general, an array can have any number of features, and the number of features contained in an array may be selected to address such considerations as, for example, experimental objectives, information-gathering objectives, and cost effectiveness. An array could be, for example, a 20×20 matrix having 400 regions, 64×32 matrix having 2,048 regions, or a 640×320 array having 204,800 regions. Advantageously, the present invention is not limited to a particular size or configuration for the array.

A linker or spacer molecule typically is a molecule inserted into the growing polymer, inserted between the surface of the substrate and the two arm linker, or inserted between the two arm linker an attached functional polymer that does not necessarily convey functionality to the a probe molecule, such as molecular recognition functionality, but instead elongates the distance between the substrate surface and the probe functionality or between two probe functionalities to enhance the exposure of the probe functionality on the surface of the substrate. The linker molecule attaches a nucleic acid molecule to the surface and can serve to space the nucleic acid molecule above the substrate surface. Typically a linker or spacer is 4 to 40 atoms long. The linker molecules may be, for example, aryl acetylene, ethylene glycol oligomers containing 2-10 monomer units (PEGs), diamines, diacids, amino acids, among others, polypeptides and polymers of amino acid derivatives such as for example, amino hexanoic acids, and combinations thereof. Diamines are molecules of the general formula $NH_2RNH_2$, where R is a branched or unbranched hydrocarbon (a molecule composed of carbon and hydrogen) having from 2 to 45 carbon atoms, wherein one or more carbon atoms may be replaced by oxygen, sulfur, silicon, and or nitrogen atoms. Examples of diamines include ethylene diamine and diamino propane. Diacids are molecules of the general formula R'OOC—R"—COOR', where R' is a branched or unbranched hydrocarbon having from 2 to 45 carbon atoms, wherein one or more carbon atoms may be replaced by oxygen, sulfur, silicon, and or nitrogen atoms, and R' is H or a hydrocarbon having from 1 to 10 carbon atoms. Typically, the OR' groups are removed during the reactions to attach the linker molecule to the substrate surface and attach the linker molecule to the nascent polymer and the resulting linker molecule has the structure —CO—R"—CO—. Alternatively, the linkers may be the same molecule type as that being synthesized (i.e., nascent polymers), such as polynucleotides, oligonucleotides, or peptides.

Optionally, the linker molecule comprises a cleavable group that can be cleaved with a cleaving reagent and that allows a synthesized polymer to be cleaved from the substrate surface. This cleaving reagent is a different reagent from the reagents used to remove protecting groups and the reagents used to remove protecting groups do not cause the cleavage of the cleavable group. The cleavable group provides the removal of synthesized polymers from the substrate surface in a controllable array region localized manner. Exemplary cleavable groups include acetic anhydride, n-acetylimidizole, isopropenyl formate, fluorescamine, 3-nitrophthalic anhydride, 3-sulfopropnic anhydride, and N-succinimidyl-4-[bis-(4-methoxyphenyl)-chloromethyl]benzoate. Alternatively, polymers can be cleaved from the entire array using chemical agents, light, or heat.

A probe or probe molecule is a small molecule or biomolecule capable of undergoing a binding or molecular recognition event with a target molecule. Molecular recognition is a specific interaction between molecules. Examples of molecular recognition events are receptor-ligand, antibody-antigen, sugar-lectin, DNA-protein, and nucleic acid hybridization reactions. A target or target molecule refers to a small molecule or biomolecule that is specifically recognized by a probe molecule through a molecular recognition event. In the case of nucleic acids, a molecular recognition event occurs, for example, when nucleic acids hybridize to complementary nucleic acids or when a molecule (a protein or peptide or other organic molecule such as a drug) binds to certain sequences of double stranded DNA but not to others.

A hybridization reaction is a process in which two single-stranded polynucleotides bind and form a stable double-stranded polynucleotide. In a hybridization event complementary nucleic acid bases pair up, and an adenine (A) pairs with a cytosine (C), and a guanine (G) pairs with a thymine (T) or uracil (U) (through, for example, standard Watson-Crick hydrogen-bonding interactions). Depending on conditions of pH, temperature, salt concentration, nucleic acids that are not absolutely complementary are able to hybridize. In general, substantially complementary nucleic acids refer to nucleic acids that have 80% or greater complementary base pairing. Highly complementary nucleic acids refer to nucleic acids having 90% or greater complementary base pairing. The proportion of the population of polynucleotides that forms stable hybrids is referred to as the degree of hybridization. In embodiments of the invention, hybridization refers to the formation of double stranded species between a probe polynucleotide and a target nucleic acid wherein the probe preferentially hybridizes target nucleic acids that are substantially complementary to the probe nucleic acid and does not hybridize nucleic acids that are not substantially complementary. The length chosen for a probe nucleic acid depends on several factors, including G/C content of the sequence, positioning of mismatched bases (if any), degree of uniqueness of the sequence as compared to the population of target nucleotides, the chemical nature of the polynucleotide (e.g., methylphosphonate backbone and phosphorothiolate), desired conditions for hybridization reaction (e.g., temperature and ionic strength of the solution).

Typically a probe molecule for single stranded DNA will be at least 5 nucleotides and less than 75 nucleotides in length. Preferably the probe is between 24 and 60 nucleotides in length. A double stranded DNA probe molecule will be comprised of two DNA strands that each have at least 5 nucleotides and less than 75 nucleotides in length. Preferably the double stranded DNA probe is comprised of two DNA strands that are each between 24 and 60 nucleotides in length.

The term stringency refers to the conditions used for a nucleic acid hybridization reaction that influence the degree to which polynucleotides hybridize, such as pH, ion concentration, and temperature. Conditions of varying stringency can be selected that allow polynucleotide duplexes to be distinguished based on their degree of mismatch. High stringency conditions (typically higher temperature, for example), only allow the most stable duplexes to form in solution and therefore selects for hybridization reactions in which the two nucleic acids are highly complementary. Conversely, at lower stringency conditions, the probability of forming a mismatched duplex is increased. Stringency conditions that allow for selection of varying degrees of complementarity between nucleic acids are generally determined empirically. Methods for preparing, isolating, and manipulating various forms of nucleic acids are well known. (See for example, Berger and Kimmel, eds., *Guide to Molecular Cloning Techniques*, Academic Press, New York, N.Y. (1987); Sambrook, Fritsch and Maniatis, eds., *Molecular Cloning: A Laboratory Manual, 2nd Ed.*, Cold Spring Harbor Press, Cold Spring Harbor, N.Y. (1989).) Additionally, techniques for hyrbidization reactions are well known and a variety of kits are commercially available for nucleic acid manipulations.

In general, nucleic acids useful in the present invention include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. Polynucleotides and nucleic acid polymers refer to polymeric forms of nucleotides and nucleotide analogs that comprise purine and pyrimidine bases, or other natural, chemically or biochemically modified, non-natural, or derivatized nucleotide bases, of any length. Polynucleotide and nucleic acid also refer to non-natural analogs of nucleic acids, such as peptide nucleic acids (nucleic acids with peptide backbones), and polyamide polynucleotides. An oligonucleotide is generally a polynucleotide having from 2 to 20 nucleotide monomer units.

A polynucleotide, including an oligonucleotide, (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including methylated nucleotides, non-naturally occurring synthetic nucleotides or modified naturally occurring nucleotides.

Typically nucleotide analogs are derived from naturally occurring nucleotides by replacing or modifying the base, the ribose, or the phosphodiester moiety. For example, structural groups can be added to the ribose or base of a nucleotide, such as a methyl, a propyl, or an allyl group at the 2'-O position of the ribose, or a fluoro group substitution at the 2-O' position. The base can also be substituted with halogens, such as bromo groups. Modified nucleotides, such as 2'-0 methyloligoribonucleotides have higher affinity for complementary polynucleotides (especially RNA) than their unmodified counterparts. Additional nucleotide analogs include deazapurines and deazapyrimidines, in which one or more nitrogen atoms of the purine or pyrimidine heterocyclic ring are replaced by carbon atoms. Some examples of base modified nucleotides include 2-amonoadenine, 5-methylcytosine, 5-(propyn-1-yl)cytosine, 5-(propynl-yl)uracil, 5-bromouracil, 5-bromocytosine, hydroxymethylcytosine, methyluracil, hydroxymethyluracil, and dihydroxypentyluracil.

The covalent bond linking the nucleotides of a polynucleotide generally is a phosphodiester bond (the sugar-phosphate backbone). However, the covalent bond also can be any of a number of other types of bonds, including a thiodiester bond, an O-methyl phosphate, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain nucleolytic activity, since the modified polynucleotides can be less susceptible to degradation.

A solid support, support, or substrate is an object having a rigid or semi-rigid surface or surfaces. In some aspects at least one surface of a solid support is planar or substantially planar. The features of an array optionally form synthesis regions that are, for example, wells, depressions, raised regions, pins, or etched trenches. In embodiments of the invention the substrate comprises a silicon wafer or a portion of a silicon wafer. A silicon wafer may also be referred to as a chip or a semiconductor substrate. A wafer or chip may be fashioned in various shapes and sizes. The chip could be overlaid or embedded with circuitry for driving electrodes, sensing voltages, microprocessors, memory functions, and input/output capabilities. In embodiments of the invention, the chip comprises at least surface-accessible electrodes and embedded circuitry for driving the electrodes and sensing voltages. A substrate may also be comprised of silicon, glass, nylon, plastic or other polymeric material, silicon nitride, metals, metal oxides, metal nitrides, or combinations thereof.

Further substrate materials useful in embodiments of the present invention include, for example, silicon, bio-compatible polymers such as, for example poly(methyl methacrylate) (PMMA) and polydimethylsiloxane (PDMS), glass, $SiO_2$ (such as, for example, a thermal oxide silicon wafer such as that used by the semiconductor industry), quartz, silicon nitride, functionalized glass, gold, platinum, and aluminum. Functionalized surfaces include for example, amino-functionalized glass, carboxy functionalized glass, and hydroxy functionalized glass. Additionally, a substrate may optionally be coated with one or more layers to provide a surface for molecular attachment or functionalization, increased or decreased reactivity, binding detection, or other specialized application. Substrate materials and or layer(s) may be porous or non-porous. For example, a substrate may be comprised of porous silicon. Additionally, the substrate may be a silicon wafer or chip such as those used in the semiconductor device fabrication industry. In the case of a wafer or chip, a plurality of arrays may be synthesized on the wafer.

Many substrate materials, such as metals, metal oxides, and $SiO_2$, have surface-attached —OH groups that are available for further reaction and molecular coupling. Further, surfaces that present —OH groups for molecular coupling can be created on substrate surfaces, through, for example, creating a thin oxide layer on a metal (such as through chemical or plasma etching processes) and depositing a thin layer of $SiO_2$ onto the surface. If the substrate surface is $SiO_2$, the surface has been coated with $SiO_2$, the surface is a metal having available —OH groups, molecules are optionally attached to the sensor surface through the use of silane linkers (or organo silane compounds). Silane linkers are molecules that have at least two different reactive groups bonded to the silane atom of the molecule: Y—R—Si—$(X)_2$. One of the reactive groups is capable of bonding to inorganic materials such as glass ($SiO_2$) and metals, the X group. These functional groups that are capable of bonding to inorganic materials are groups such as methoxy, ethoxy, chlorine, and silanolic hydroxyl groups. The second functional group is a group such as a vinyl, an epoxy, a methacryl, an amino, a mercapto, or a carboxylic acid group that is capable of forming a chemical bond to an organic material, the Y group. The R group is typically an organic group comprised of from 1 to 10 carbon atoms, such as a straight chain or branched alkane. For example, a silanating agent, such as hydroxypropyltriethoxysilane can be vapor deposited or supplied in a solution to the surface to be silanated. After reaction, the surface presents a —OH group for further molecular coupling. Metal surfaces such as nickel, palladium, platinum, titanium dioxide, aluminum oxide, indium tin oxide, copper, iridium, aluminum, titanium, tungsten, rhodium or other surface having available hydroxy groups or other similar surface groups can also be silanated for further attachment of molecules. A very thin layer of oxide can be created on a metal surface, for example, by etching the metal surface with an oxygen plasma or through damascene processes.

Nucleotides attached to a variety of functional groups may be commercially obtained (for example, from Molecular Probes, Eugene, Oreg.; Quiagen (Operon), Valencia, Calif.; and IDT (Integrated DNA Technologies), Coralville, Iowa) and incorporated into oligonucleotides or polynucleotides. Oligonucleotides may be prepared using commercially available oligonucleotide synthesizers (for example, Applied Biosystems, Foster City, Calif.). Additionally, modified nucleotides may be synthesized using known reactions, such as for example, those disclosed in, Nelson, P., Sherman-Gold, R, and Leon, R, "A New and Versatile Reagent for Incorporating Multiple Primary Aliphatic Amines into Synthetic Oligonucleotides," *Nucleic Acids Res.*, 17:7179-7186 (1989) and Connolly, B., Rider, P. "Chemical Synthesis of Oligonucleotides Containing a Free Sulfhydryl Group and Subsequent Attachment of Thiol Specific Probes," *Nucleic Acids Res.*, 13:4485-4502 (1985). Alternatively, nucleotide precursors may be obtained commercially containing various reactive groups, such as biotin, hydroxyl, sulfhydryl, amino, or carboxyl groups.

In general, peptides are polymers of amino acids, amino acid mimics or derivatives, and/or unnatural amino acids. The amino acids can be any amino acids, including α, β, or ω-amino acids and modified amino acids. When the amino acids are α-amino acids, either the L-optical isomer or the D-optical isomer may be used. In general, an amino acid contains an amine group, a carboxylic group, and an R group. The R group can be a group found on a natural amino acid or a group that is similar in size to a natural amino acid R group. Additionally, unnatural amino acids, for example, β-alanine, phenylglycine, homoarginine, aminobutyric acid, aminohexanoic acid, aminoisobutyric acid, butylglycine, citrulline, cyclohexylalanine, diaminopropionic acid, hydroxyproline, norleucine, norvaline, ornithine, penicillamine, pyroglutamic acid, sarco sine, and thienylalanine are also contemplated by the embodiments of the invention. These and other natural and unnatural amino acids are available from, for example, EMD Biosciences, Inc., San Diego, Calif.

A peptide is a polymer in which the monomers are amino acids, a group of molecules which includes natural or unnatural amino acids, amino acid mimetics, and amino acid derivatives, which are generally joined together through amide (peptide) bonds. A peptide can alternatively be referred to as a polypeptide. Peptides contain two or more amino acid monomers, and often more than 50 amino acid monomers (building blocks).

A protein is a long polymer of amino acids linked via peptide bonds and which may be composed of one or more polypeptide chains. More specifically, the term protein refers to a molecule comprised of one or more polymers of amino acids. Proteins are essential for the structure, function, and regulation of the body's cells, tissues, and organs, and each protein has unique functions. Examples of proteins include some hormones, enzymes, and antibodies.

Figure 3:
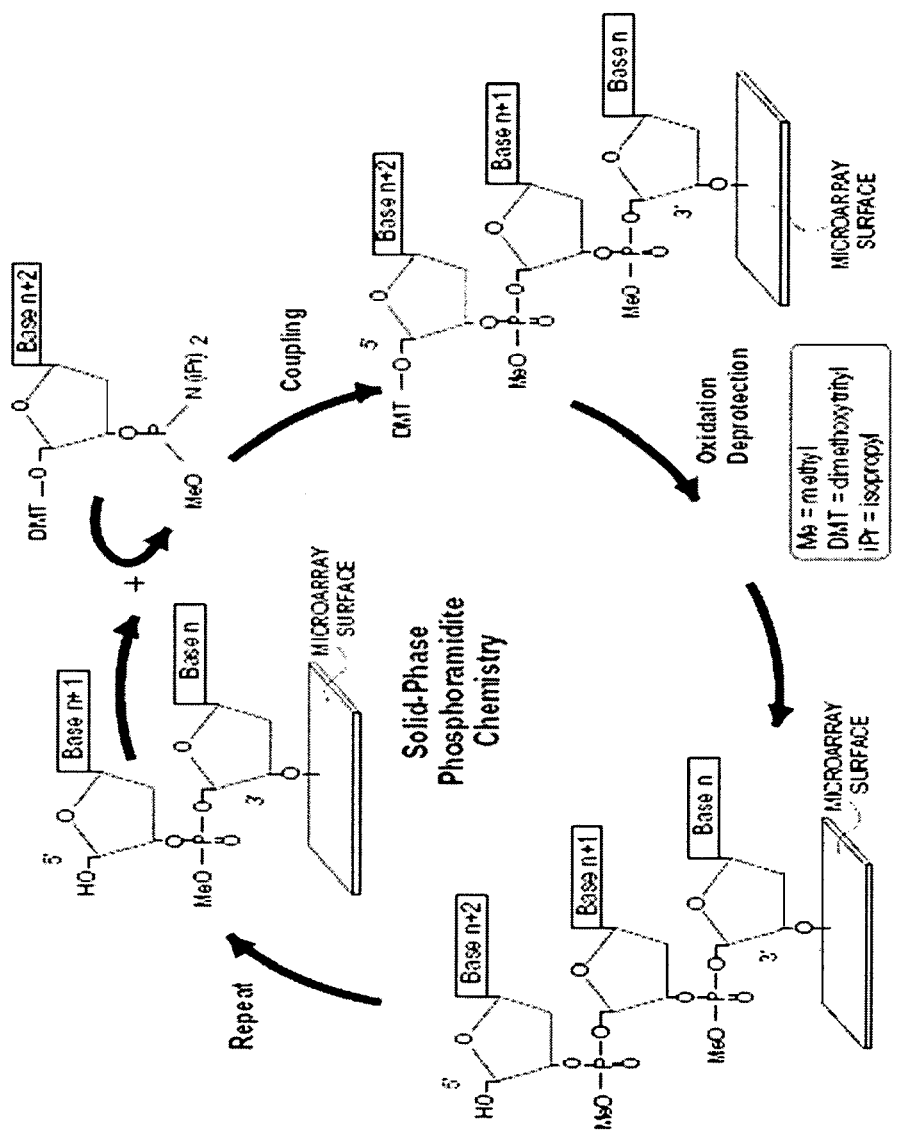
FIG. 3 diagrams a method for solid-phase nucleic acid synthesis that can be used to controllably build nucleic acid molecules having a desired sequence on a solid surface.

A monomer addition cycle is a series of chemical reactions that result in the addition (or covalent attachment) of a monomer to a growing polymer chain or linker molecule. For example, the following steps typically comprise a common method used to synthesize a polynucleotide on a solid support (i.e., phosphoramidite-based solid phase polynucleotide synthesis). In this example, the monomer is a nucleotide and the polymer is a polynucleotide. Referring now to FIG. 3, a first step in the polynucleotide synthesis is the deprotection of the surface-attached polymer growth site through removal of the DMT group from, for example, a 5'-protected nucleotide wherein the 5'-hydroxyl is blocked through the covalent attachment of DMT. The deprotection is accomplished using a protic acid (for example, a protic acid such as trichloroacetic acid, dichloroacetic acid, or an electrochemically generated acid). The substrate optionally is then washed to remove the cleaved protecting group and other reagents and mobile reaction products (with, for example, acetonitrile). A molecule, such as a phosphoramidite nucleotide (a nucleotide having attached protecting groups: a DMT on the 5'-OH group, a benzoyl or isobutyryl on exocyclic amines associated with the nucleotide base (not shown), a diisoprotylamino and a 2-cyanoethyl group on the phosphate), optionally activated with tetrazole, is then coupled to the surface-attached deprotected molecule. Optionally unreacted surface-attached deprotected molecules are capped to prevent further participation in subsequent monomer addition cycles. The trivalent phosphate trimester linkage is converted to a pentavalent phosphate triester through oxidation with, for example, iodine, and the pentavalent phosphate triester is converted to a phosphodiester through reaction with ammonium hydroxide. Protecting groups associated with the base group of the nucleoside can be removed after synthesis of the polynucleotide is complete.

Any unreacted deprotected chemical functional groups may be capped at any point during a synthesis reaction to avoid or to prevent further bonding at such molecule. Once the first polymer that is attached to a first arm of the two arm linker is complete, it can be capped to prevent further reactivity. In general, capping reagents can be a reagent that prevents further reactivity at the site of polymer chain formation such as, for example, an acid anhydride without further reactive functionalities. Capping groups cap deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfoproponic anhydride.

A monomer addition cycle used to create a peptide is as follows. An amino acid having an amino protecting group is coupled to a surface presenting a —NH$_2$ group. In this example, the amino acid is N-protected with a BOC protecting group. The coupling reaction is performed in a solution of 1-hydroxybenzotriazole (HOBt) and diisopropylcarbodiimide (DIC) in N-methyl pyrrolidone (NMP). Unreacted amine groups are capped using an acetic anhydride (Ac$_2$O) solution in dimethylformamide (DMF). Areas of an array are activated toward further monomer addition (amino acid addition) by removing the BOC protecting group (with acid) in the selected regions. A second amino acid is then coupled in the activated (deprotected) regions. By repeating the monomer addition process using selected amino acid monomers, peptides of desired sequence and length in selected regions upon the substrate surface are produced.

An array of polymer molecules on a substrate or on an array of electrodes may be created by several methods. For example, the synthesis of an array of nucleic acid molecules or peptides on a substrate can be accomplished using photochemical synthesis methods, photoresist synthesis methods, and electrochemical synthesis methods. In photochemical synthesis techniques, protecting groups that prevent polymer growth are removed photochemically (using electromagnetic radiation).

In photoresist synthesis methods, a photoresist is applied over the array synthesis area and the photoresist is patterned with electromagnetic radiation to expose areas in which the polymer chain is to be extended by monomer addition or to protect regions in which the polymer chain is not to be extended from monomer addition. In an exemplary synthesis method, photoresists such as poly(methyl methacrylate) (PMMA) are provided with sulfonium, polonioum, or halonium salts that generate an acid upon exposure to UV light. The photochemically generated acid deprotects the protected polymer chain (for example, through the removal of a DMT group) to allow the addition of a monomer to the growing end of the unprotected polymer chain. Optionally, the photoresist layer also includes a photosensitizer, such as a benzophenone, a thioxanthenone, an anthraquinone, a fluorenone, an acetophenone, or perylene. In the case of a photosensitizer, the generation of the protecting group removal reagent may occur through the absorption of light by a photosensitizer followed by reaction of the photosensitizer with the protecting group removal reagent precursor (the molecule capable of generating an acid upon activation), energy transfer from the photosensitizer to the cleavage reagent precursor, or a combination of two or more different mechanisms. After the photoresist is removed, the polymer chain in the light-exposed regions is available for monomer addition. Through repeated cycles of photoresist coating, light exposure (optionally through a mask to pattern the photoresist), and monomer addition, an array of polymers that have different known sequences is built on the surface of a substrate.

Optionally, a fully formed polymers (such as peptides or antibodies) may be coupled to an arm of the trifunctional linker molecule. A variety of coupling methods are known in the art. See for example, for example, the types of groups disclosed in Aslam, M. and Dent, A., *Bioconjugation: Protein Coupling Techniques for the Biomedical Sciences*, Grove's Dictionaries, Inc., 301-316 (1998).

The electrodes of an array of electrodes optionally are used to synthesize polymers on the surface of some or all of the solution-exposed electrodes. For synthesis the electrodes are used to create an acidic or basic region around the electrode surface. The acid or base causes deprotection of the growing polymer chain and allows monomer addition. Optionally, confinement electrodes of opposite polarity or floating separate attachment electrodes are provided to confine the acid or basic region produced and prevent drift to surrounding electrodes that may not be activated for synthesis. Further optionally, a set of two latches are provided at each electrode capable of being activated for polymer synthesis to allow the electrode to exist in multiple states: driven by a first voltage, driven by a second voltage, or floated during the synthesis cycle.

Electrochemical reagents are reactive species that can be generated electrochemically at an electrode through an oxidation or reduction process. Electrochemical reagents can be generated at an electrode by supplying a minimum voltage that corresponds with the oxidation or reduction potential of the desired species in solution. Species such as acids ($H^+$) and bases ($OH^-$) can be generated electrochemically. Molecules that can be used to generate an acid electrochemically that can used to deprotect a growing nucleic acid polymer attached to an electrode surface (e.g., remove a DMT group) include, for example hydroquinone that is converted to benzoquinone upon oxidation thereby releasing two protons ($H^+$) and a hydroquinone that is converted to anthraquinone upon oxidation thereby releasing two protons ($H^+$) (a non-aqueous system).

An electrochemical reagent can be generated at a solution-accessible electrode by applying sufficient electrical potential to an electrode. The electrochemical reagent is capable of removing a protecting group from the growing end of a polymer being synthesized on the electrode. In this instance the electrochemical reagent is a deprotecting agent. In other reactions, the electrochemical reagent may be an intermediate in the formation of the deprotecting agent.

Voltage sources for the electrodes can be internally multiplexed from external source(s) through digital control and can optionally be applied in parallel to a large array of electrodes. In operation, voltages are applied to a programmed selection of electrodes as a solution containing a monomer is supplied to the exposed electrodes. An applied voltage creates an acidic or basic region and allows polymer growth at the selected electrode. Through selection of electrodes and choice of monomer to supply, polymers of known desired sequence are synthesized at the electrodes.

Electrode surfaces typically present —OH groups for molecular coupling, but can also be treated or functionalized to provide, for example, —OH groups for further molecular attachment. A spacer or linker molecule can be coupled to the surface —OH group before a two arm linker having orthogonal protection is coupled. One arm of the two-arm linker is selectively deprotected and a polymer is synthesized on the arm according to solid-phase synthesis techniques. Electrodes are individually activated to form a deprotecting agent, such as an EGA. A solution containing the desired monomer to be coupled to the growing polymer chain is provided and the monomer is coupled to the growing chain on electrodes that have polymer chains that have been deprotected. The cycles of deprotection and coupling are repeated to form a polymer chain having a desired sequence. The second arm is then deprotected and a second polymer is built on the arm according to solid-phase synthesis techniques.

Electrode arrays are optionally used both to perform solid-phase polymer synthesis on the surface of the electrode and to detect the presence of probes and molecules that have bound to the probes on the surface of the electrode. For example, for an electrode functionalized with a probe nucleic acid molecule exposed to a solution containing a target nucleic acid molecule, the presence of double stranded nucleic acids on the surface of the electrode is indicative of the occurrence of a hybridization reaction. For an electrode functionalized with dsDNA, a change in capacitance at the surface of an electrode is indicative of a binding event associated with the dsDNA. Electronic detection provides the ability to monitor synthesis and hybridization reactions in real time without the use of labels. Since no wash is required to remove unbound labeled analytes, binding kinetics can be monitored using dynamic measurements at the solid-solution interface.

Electronic detection is the detection of a molecule through a measurement of voltage, resistance, and or current characteristics of an electronic sensor in the presence of the molecules to be detected. Optionally, the electronic signal measured in the presence of the molecule to be detected is compared to an electronic signal measured in the absence of the molecules to be detected.

A wafer refers to a semiconductor substrate used in the fabrication of integrated circuits and other microdevices and is for example a substrate comprised of a silicon crystal. The wafer serves as a substrate for a micoelectronic device having a large number of electronic features that is built through the use of nano and microfabrication techniques such as deposition of various materials, such as conductors, semiconductors, and insulators, photolithographic patterning, etching, and ion implantation. An array of electrodes can be equipped with circuitry for individually addressing the electrodes, driving the electrodes at selected voltages (or set current values corresponding to the desired voltage), memory for storing voltage current information to be supplied to the electrodes, memory and microprocessors for measuring electrode characteristics, differential amplifiers, field effect transistors (direct and floating gate). Alternatively, one or more of these functions can be performed by an attached computer system.

Figure 4:
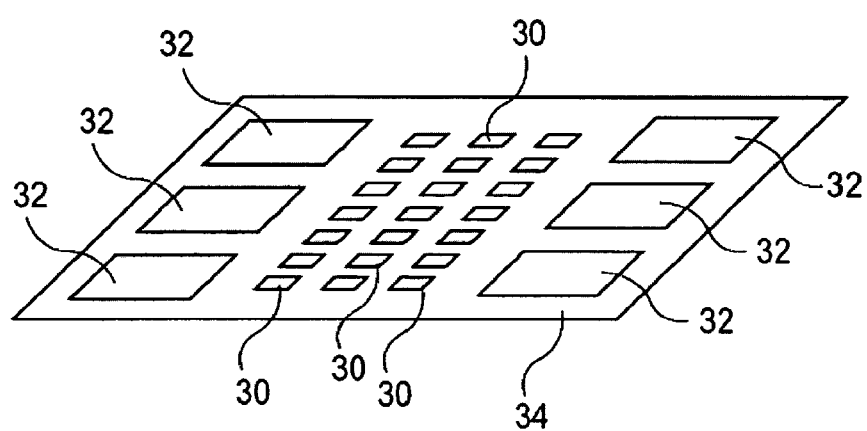
FIG. 4 is a simplified diagram of an exposed electrode array that can be used to synthesize polymers on the electrodes and to detect molecular recognition events using the array of electrodes.

FIG. 4 provides a simplified diagram showing an array of exposed sensing and reference electrodes 30 and drive electrodes 32 on a substrate 34. Probe molecules (not shown) are attached to the sensing and or reference electrodes. The reference electrode may or may not have a similar or different affinity probes attached. The sensing electrodes optionally have a plurality of probe molecules attached wherein the probe molecules attached to one sensing electrode are different from the probe molecules attached to a different sensing electrode. Drive electrodes 32 are typically larger in surface area than the micron or sub-micron scale sensing and reference electrodes 30. Electronics associate with driving the electrodes and signal handling (sensing and referencing capacity) (not shown) are located in the substrate 34. An integrated charge value from an electrode is converted to a voltage value through a two stage amplifier. An internal (not exposed) monolithic NMOS or metal-insulator-metal capacitor is optionally connected to the amplifier via an internal switch and used as a reference capacitor.

Optionally, an integrating charge amplifier is connected to an electrode (or the electrodes comprising the array) and configured to detect capacitance changes at the electrode surface. A differential amplifier (or a differential-input single-ended output amplifier) is a device that amplifies the difference between two input signals (−) and (+). Optionally, the integrating charge amplifier includes a drive circuit that is capable of providing voltage pulses which can be supplied, for example, as a square, sine, or sawtooth wave form to a solution-accessible (exposed) electrode. The integrating charge amplifier optionally also includes an input that is from an exposed sensing electrode and another input from a solution-exposed or unexposed reference electrode.

A device including one or more integrating charge amplifiers is preferably configured to measure the integrated charge and effective capacitance at the analyte-electrode interface. A change in integrated charge or effective capacitance can then be used to ascertain whether a hybridization reaction has occurred (i.e., whether analytes have bound at the electrode surface or to the affinity probe attached to the electrode surface). An array of integrating amplifiers and a corresponding electrode array are optionally fabricated on the same substrate. The substrate may also include synthesis and detection drive circuits, logic for switching, latches, memory, input/output devices.

Figure 5:
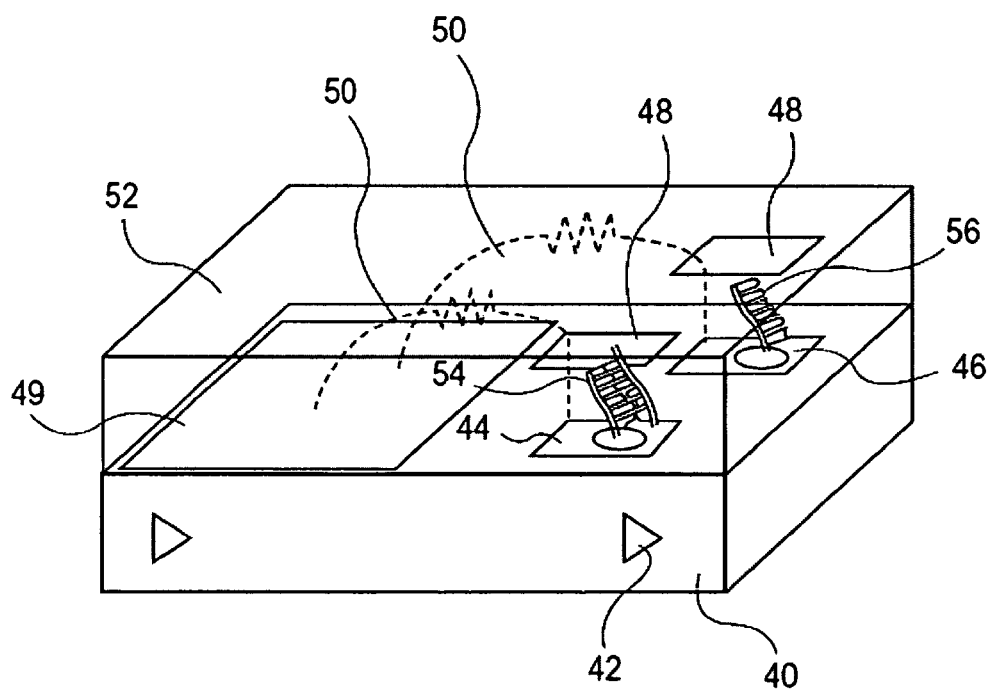
FIG. 5 provides a schematic of the electronic detection of a molecular recognition event using an array of exposed electrodes.

FIG. 5 provides a schematic of an exemplary electronic device capable of detecting a hybridization event between a surface-attached DNA probe molecule and a target molecule. The electronic molecular detection device has a substrate 40 that houses electronics for detecting 42 (as described more fully herein), exposed sensing electrodes 44, exposed reference electrode 46, and drive electrode 49. The electrodes 44, 46, and 49 are connected to electronics through physical electrical connections. In FIG. 5, dotted lines 50 demonstrate resistive and capacitive paths (virtual capacitive plates 48 are shown) established in the conductive matrix of buffer solution 52 and insulating affinity probe/analyte layer 54 on the electrode 44. The probe/analyte layer 54 is not to scale with respect to the electrode size and only one probe/analyte complex is shown (for simplicity) where many would typically be attached to an electrode surface. In FIG. 5, the electronic detection device can be operated in differential detection mode, in which both reference electrodes 46 and sensing electrodes 44 have attached affinity probes 54 and 56. The electronics 42 comprising a differential charge amplifier provide differential sensing data to an output amplifier and A/D or analog output.

For measurements of effective capacitance, the analyte is preferably provided in a conductive solution that provides a conductive path between the driving and the integrating electrodes of the amplifier. A conductive solution comprises for example, an aqueous solution having an ionic concentration or a conductive gel. A preferred method for operating a device including one or more integrating charge amplifiers includes providing a voltage pulse through the drive electrode to the conductive matrix. This pulse can be applied to the matrix with respect to an integrating electrode and the charge is accumulated on the integrating electrode over a fixed time.

Figure 6:
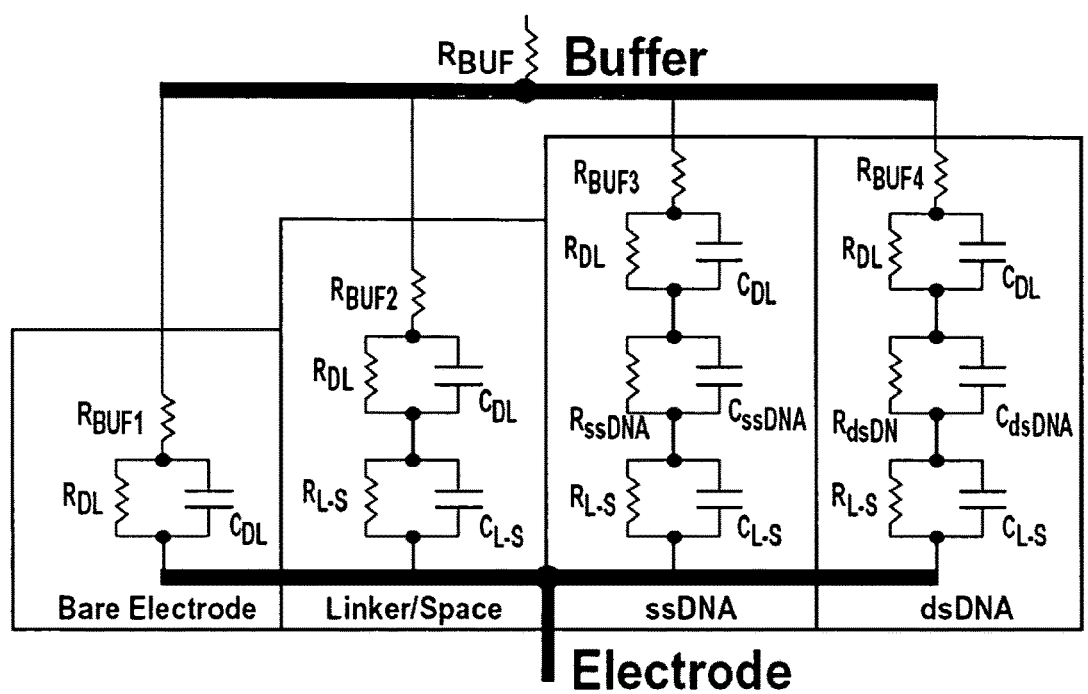
FIG. 6 shows a circuit model for the electronic detection of a molecular recognition event on an electrode.

The measured capacitance is established by the fixed sensing electrode, the dielectric formed by the attachment chemistry, attached probe, and bound analyte (if present), and a virtual parallel plate formed above the sense electrodes by the charge/ion distribution in the matrix. The measured capacitance is a function of the electrode area, the dielectric constant, and the distance of the virtual plate from the sensing electrode. Analytes binding to the electrode or the attached affinity probe will change the dielectric constant and or the distance between the virtual plate and the sensing electrode, thereby changing the effective capacitance and accumulated charge on the sensing electrode when a voltage is applied. The area and distance to the drive electrode are not material since the conductive matrix carries the voltage to the virtual plate. FIG. 4 provides a theoretical circuit model for the electronic detection of a hybridization reaction. In FIG. 6, ssDNA (single stranded DNA) represents the probe attached to the electrode and dsDNA (double stranded DNA) represents the probe hybridized to a target analyte. Any capacitance contributed by the drive electrode is in series with the measured capacitance and is small owing to the large electrode area.

Optionally, to compensate for noise that may be present (low frequency noise, thermal noise, etc.) a calibrating reference pulse is applied to an internal test capacitor to normalize the response of the amplifier during each measurement cycle. The output of this amplifier can then be digitized and post-processed. Post-processing comprises a software algorithm to remove random noise, slopes, or other artifacts from the data. Parameters can be determined experimentally by characterizing the various contributing parameters, such as electrode size, drive voltage, and environmental conditions such as temperature and analyte binding concentration.

Optionally, individually addressable sensing electrode arrays of various effective areas are created to increase the detection range of the amplifier to various concentrations of target in the solution. A large array of driving electrodes can be created to allow close coupling of driving voltage to the solution. Since the drive electrode capacitance is in series with the sense electrode plus probe or probe/target complex through the solution, preferably the driving electrode area is larger than the sensing electrode area to reduce parasitic effects. A system comprised of a large capacitor in series with a small capacitor is dominated by the small capacitor. In the case of a large capacitor in series with a small capacitor, $1/C_{series} = 1/C_{integrated} + 1/C_{drive}$ and this approaches $1/C_{integrated}$ in value as $C_{drive}$ gets large.

The exposed reference electrode allows for common mode noise rejection by inputting to one input the amplifier signal representing the same environmental conditions (pH, temperature, ion concentration, presence or absence of non-binding analytes, etc.). Alternatively, the reference capacitor can be exposed to air or covered to establish an absolute reference.

Figure 7:
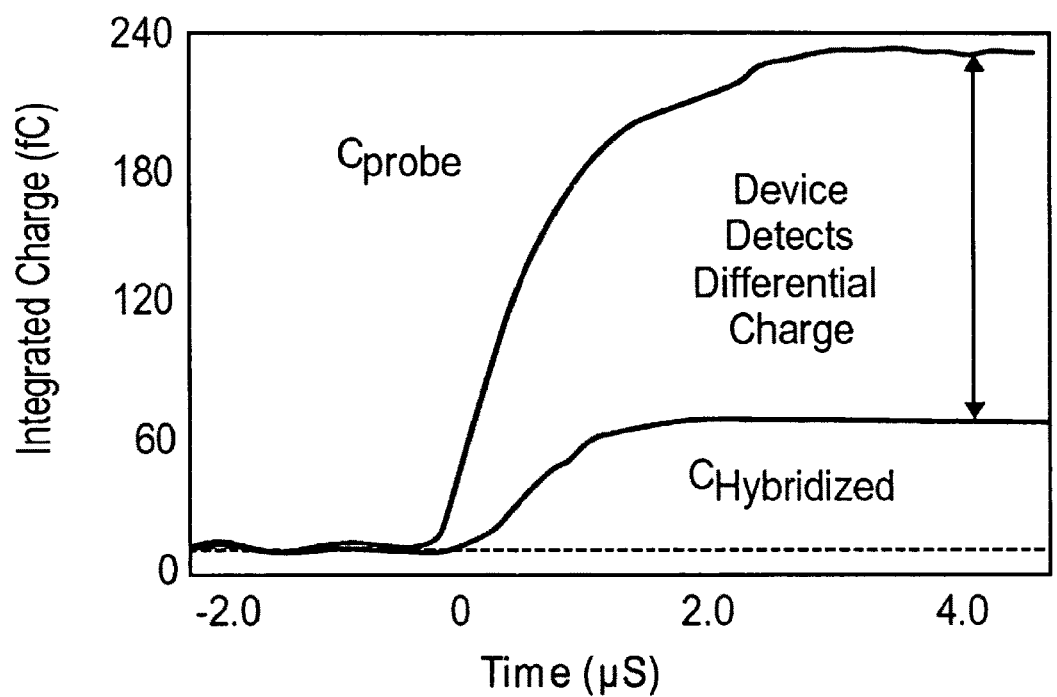
FIG. 7 provides a graph showing the electronic detection of a molecular recognition event, such as a DNA hybridization event, using exposed electrodes.

FIG. 7 provides graphs the operation of an exemplary device such as the exemplary devices shown in FIGS. 4 and 5 in the detection of a molecular recognition event at the surface of an electrode between a bound nucleic acid probe and a complementary nucleic acid molecule. FIG. 7 shows the measurement of integrated charge on two electrodes, the electrode having only the probe attached (trace labeled $C_{probe}$) and the electrode having an attached probe that is hybridized to a complementary nucleic acid (trace labeled $C_{hybridized}$). An integrating charge amplifier is used to detect capacitance on the functionalized electrode surface. A dynamic measurement at the solid-solution interface is obtained by applying a pulse to the functionalized electrode and integrating the current flow response over time as the capacitor discharges.

A pulse of voltage is applied to the solution with respect to an integrating electrode and charge is accumulated on the electrode over a fixed time. A calibrating reference pulse can be applied to the solution through an internal test capacitor to normalize the response of the amplifier during each measurement cycle. A two-stage integrating charge amplifier converts measured charge to voltage.

The measurement of change in capacitance at the sensing electrode can be accomplished in the following manner. The change can be detected with respect to the exposed reference capacitor when the reference electrode is exposed to the same solution as the sensing electrode. Optionally, a nucleic acid molecule that has similar electrical characteristics as the affinity probe attached to the sensing electrode but that does not bind to a target analyte in solution is attached to the reference electrode. A change in integrated charge is measured as binding occurs on the sensing electrode (binding to the probe attached on the sensing electrode) and no change is measured on the reference electrode. Alternatively, two measurements of the same electrode, before and after analyte binding, can be compared to determine the change in integrated charge resulting from target analyte binding. In this example, a measurement of the electrode at a previous time serves as the reference. Data is optionally gathered and analyzed using a computer.

In an additional alternative, the reference electrode can be configured to take direct capacitance measurements at the sensing electrode (non-differential mode). The reference electrode is covered with a dielectric substance (such as, for example, epoxy) or a dielectric layer (such as, for example, silicon dioxide) or left exposed to air. The signal from the electrode is compared to an open circuit thereby establishing an absolute reference for measurement.

The solution-accessible (or exposed) electrodes used in embodiments of the invention are made from metals, combinations of metals, or other conducting materials. For example, an electrode may be made from, for example, platinum, palladium, nickel, copper, iridium, aluminum, titanium, tungsten, gold, rhodium, as well as alloys of metals, conducting forms of carbon, such as glassy carbon, reticulated vitreous carbon, basal plane graphite, edge plane graphite, graphite, indium tin oxide, conducting polymers, metal doped conducting polymers, conducting ceramics, and conducting clays. A functionalized electrode is an electrode having a probe molecule that has a specific affinity for a target molecule attached to the electrode surface. An unfunctionalized electrode is an electrode having no probe molecule attached or an attached molecule that has no specific chemical affinity for a target molecule to be analyzed.

Electrodes are connected to sensing and driving circuitry according to known methods. For example, CMOS (complementary metal oxide semiconductor) circuitry could be used, magnetic radiation-addressable switches, direct connections from an electrode to a bond pad on the perimeter of a semiconductor chip, and or combinations thereof. Data is optionally gathered and analyzed using a computer.

Electrodes are connected to a source capable of providing voltage and current. For example, electrodes that form an array are connected to CMOS (complementary metal oxide semiconductor) switching circuitry, radio frequency (RF) and microwave addressable devices, light addressable devices, and or metal lines leading to the perimeter of the array. In embodiments of the invention, CMOS switching circuitry involves the connection of each of the electrodes to a CMOS transistor switch and provides the ability to individually address electrodes comprising an array. The switch is accessed by sending an electronic address signal down a common bus to SRAM (static random access memory) circuitry associated with the electrode. Radio and microwave frequency addressable switches involve the switching between on and off states through the use of a microwave or RF radiation. RF and microwave frequency switches can be tuned to receive a particular frequency or modulation frequency and switch without the use of array-based switching logic. Light addressable switches are moved between on and off positions by light in the ultraviolet through infrared frequency ranges. An electromagnetic signal can be spatially localized to provide switching.

Optionally, an integrating charge amplifier is connected to an electrode (or the electrodes comprising the array) and configured to detect capacitance changes at the electrode surface. A differential amplifier (or a differential-input single-ended output amplifier) is a device that amplifies the difference between two input signals (−) ad (+). Optionally, the integrating charge amplifier includes a drive circuit that is capable of providing voltage pulses which can be supplied, for example, as a square, sine, or sawtooth wave form to a solution-accessible (exposed) electrode. The integrating charge amplifier optionally also includes an input that is from an exposed sensing electrode and another input from a solution-exposed or unexposed reference electrode.

A device including one or more integrating charge amplifiers is preferably configured to measure the integrated charge and effective capacitance at the analyte-electrode interface. A change in integrated charge or effective capacitance can then be used to ascertain whether a hybridization reaction has occurred (i.e., whether analytes have bound at the electrode surface or to the affinity probe attached to the electrode surface). An array of integrating amplifiers and a corresponding electrode array are optionally fabricated on the same substrate. The substrate may also include synthesis and detection drive circuits, logic for switching, latches, memory, input/output devices.

The invention claimed is:

1. An array of DNA molecules, comprising:
    a support structure that has a surface wherein the surface comprises regions and the regions comprise a plurality of DNA polymers that are attached to the surface of the support structure,
    wherein at least one of the regions comprises DNA polymers and amino acid polymers,
    wherein a DNA polymer and an amino acid polymer are attached to the substrate surface through one trifunctional linker molecule,
    wherein the trifunctional linker molecule has three sites for attachment and wherein a the DNA polymer is attached to one of the three sites, the amino acid polymers is attached to a second of the three sites, and a third site is attached to the surface of the substrate.

2. The array according to claim 1 wherein the array comprises 1,000 to 10,000 regions.

3. The array according to claim 1 wherein the array comprises 100 to 1,000 regions.

4. The array according to claim 1 wherein a region of the array is less than 100 µm$^2$.

5. The array according to claim 1 wherein the DNA polymers each comprise from 5 to 50 nucleic acids.

6. The array according to claim 1 wherein the DNA polymers each comprise from 10 to 30 nucleic acids.

7. The array according to claim 1 wherein the DNA polymers are attached to the trifunctional linker through a spacer group and the spacer group comprises a polyethylene glycol.

8. The array according to claim 1 wherein the trifunctional linker is attached to the substrate through a spacer group comprising polyethylene glycol.

* * * * *

UNITED STATES PATENT AND TRADEMARK OFFICE
CERTIFICATE OF CORRECTION

PATENT NO. : 10,294,526 B2
APPLICATION NO. : 15/687758
DATED : May 21, 2019
INVENTOR(S) : Gao et al.

Page 1 of 1

It is certified that error appears in the above-identified patent and that said Letters Patent is hereby corrected as shown below:

In the Claims

Column 18, Line 62, Claim 1, after "wherein", delete "a"

Signed and Sealed this
Fourteenth Day of April, 2020

Andrei Iancu
*Director of the United States Patent and Trademark Office*